(12) United States Patent
Knoll et al.

(10) Patent No.: US 10,595,391 B2
(45) Date of Patent: *Mar. 17, 2020

(54) PLASMA GENERATION

(71) Applicant: FOURTH STATE MEDICINE LTD., Heslemere (GB)

(72) Inventors: Aaron Knoll, Farnborough (GB); Thomas Harle, Pulborough (GB); Peter Shaw, Guildford (GB); Thomas Frame, Soberton (GB); Thomas Wantock, Godalming (GB)

(73) Assignee: FOURTH STATE MEDICINE LTD., Heslemere (GB)

( * ) Notice: Subject to any disclaimer, the term of this patent is extended or adjusted under 35 U.S.C. 154(b) by 129 days.

This patent is subject to a terminal disclaimer.

(21) Appl. No.: 15/524,344

(22) PCT Filed: Nov. 2, 2015

(86) PCT No.: PCT/GB2015/053294
§ 371 (c)(1),
(2) Date: May 4, 2017

(87) PCT Pub. No.: WO2016/071680
PCT Pub. Date: May 12, 2016

(65) Prior Publication Data
US 2017/0339776 A1    Nov. 23, 2017

(30) Foreign Application Priority Data
Nov. 4, 2014   (GB) .................................. 1419636.4

(51) Int. Cl.
*H05H 1/34* (2006.01)
*A61B 18/04* (2006.01)
(Continued)

(52) U.S. Cl.
CPC .............. *H05H 1/34* (2013.01); *A61B 18/042* (2013.01); *A61L 2/0011* (2013.01); *A61L 2/14* (2013.01);
(Continued)

(58) Field of Classification Search
CPC .......... A61B 18/042; A61B 2018/0047; A61B 2018/00577; A61B 17/00;
(Continued)

(56) References Cited

U.S. PATENT DOCUMENTS 5,177,338 A * 1/1993 Sakuragi ............ B23K 35/0205
                                                     219/119
5,486,674 A * 1/1996 Lynum ..................... H05H 1/32
                                                     219/121.48
(Continued)

*Primary Examiner* — Wei (Victor) Y Chan
(74) *Attorney, Agent, or Firm* — Lando & Anastasi, LLP

(57) ABSTRACT

A plasma torch having an open end from which a plasma plume is emitted in use is disclosed. The plasma torch includes a central cathode rod, a grounded conductive tube having an open end and being arranged around the cathode and spaced therefrom to form a first cylindrical cavity open at one end; and a high voltage electrode having a dielectric barrier material at a radially inward-facing surface thereof and being arranged around the grounded conductive tube and spaced apart therefrom to form a second annular cylindrical cavity open at one end. A constant direct current (DC) electrical power plus a high voltage pulsed electrical power is provided to the cathode producing an arc discharge in the first cavity between the cathode and grounded tube to generate a central thermal plasma emitted at an open end of the first cylindrical cavity. A high voltage alternating current electrical power or pulsed electrical power is provided to the high voltage electrode producing a dielectric barrier discharge in the second annular cylindrical cavity to generate a non-thermal plasma emitted from an open end of the second cavity as a halo around the central thermal plasma.

23 Claims, 7 Drawing Sheets

(51) Int. Cl.
*A61L 2/14* (2006.01)
*H05H 1/24* (2006.01)
*A61L 2/00* (2006.01)
*H05H 1/48* (2006.01)
*A61L 2/26* (2006.01)
*A61N 1/04* (2006.01)
*A61N 1/44* (2006.01)
*A61B 18/00* (2006.01)
*A61N 1/32* (2006.01)

(52) U.S. Cl.
CPC .............. *A61L 2/26* (2013.01); *A61N 1/0424* (2013.01); *A61N 1/44* (2013.01); *H05H 1/2406* (2013.01); *H05H 1/48* (2013.01); *A61B 2018/00452* (2013.01); *A61B 2018/00476* (2013.01); *A61B 2018/00577* (2013.01); *A61B 2018/00595* (2013.01); *A61L 2202/11* (2013.01); *A61L 2202/21* (2013.01); *A61L 2202/24* (2013.01); *A61N 1/0468* (2013.01); *A61N 1/328* (2013.01); *H05H 2001/3484* (2013.01)

(58) Field of Classification Search
CPC ........... A61B 2017/00761; A61B 2018/00452; A61B 2018/00476; A61B 2018/00595; A61L 2/0011; A61L 2/14; A61L 2202/11; A61L 2202/21; A61L 2202/24; A61L 2/007; A61L 2/26; H05H 1/2406; H05H 1/34; H05H 2001/3447; H05H 2245/122; H05H 2277/10; H05H 1/28; H05H 1/3405; H05H 1/48; H05H 2001/3484; A61N 1/0468; A61N 1/0424; A61N 1/328; A61N 1/44; A61F 13/00051
USPC .................................................... 315/111.21
See application file for complete search history.

(56) References Cited

U.S. PATENT DOCUMENTS

| | | | |
|---|---|---|---|
| 2004/0044342 A1 | 3/2004 | Mackay | |
| 2011/0108726 A1* | 5/2011 | Hiraoka | H05H 1/2406 250/282 |
| 2011/0142724 A1* | 6/2011 | Moon | H05H 1/48 422/186 |
| 2015/0050614 A1* | 2/2015 | Liu | A61C 19/00 433/32 |
| 2015/0056107 A1* | 2/2015 | Hancock | A61L 2/14 422/186 |
| 2015/0129560 A1* | 5/2015 | Muramatsu | B23K 9/173 219/74 |
| 2015/0334818 A1* | 11/2015 | Namburu | H05H 1/34 219/121.51 |
| 2015/0343555 A1* | 12/2015 | Gullotta | B23K 10/006 219/121.54 |
| 2016/0219688 A1* | 7/2016 | Carletti | H05H 1/28 |

* cited by examiner

PLASMA GENERATION

RELATED APPLICATIONS

This application is a National Stage Application of International Patent Application WO2016071680, PCT/GB2015/053294, filed Nov. 2, 2015, which claims priority to GB Patent Application No. 1419636.4, filed Nov. 4, 2014, all of which is incorporated by reference.

FIELD OF THE TECHNOLOGY

The present invention relates generally to plasma generation. In particular, the present invention relates to plasma torches, electrical power generator unit, control modules and methods of operation thereof for producing a cooperative plasma plume having a central thermal plasma blade and a non-thermal plasma halo. The plasma plume finds particular utility in cosmetic treatment of skin, in surgical treatment of wounds and in sterilization of objects in industrial processes.

BACKGROUND

Surface ablation of biological tissue is a process used in a variety of medical procedures. An ablation process may be used to remove unwanted tissue and can also be used, in certain tissues, to stimulate or induce regeneration and renewal.

Various cosmetic treatments are known and widely used that attempt to reduce the effects of ageing through surface ablation or other minor trauma of the skin to induce regeneration thereof. The skin is made up of two main layers, the dermis and the epidermis which provides the exposed surface. The epidermis comprises layers of maturing skin cells one on top of the other, with the outermost layer being a layer of dead cells that is shed and replaced by layers underneath as they reproduce. These cosmetic procedures aim to improve the appearance of patient's skin with the intention of, for example, reducing visible fine lines and wrinkles, 'rejuvenating' the skin to remove pigment spots and providing a smoother finish, and improving the appearance of scar tissue, such as scars resulting from acne.

These cosmetic procedures typically fall into three categories: mechanical procedures, chemical procedures and laser procedures.

'Mechanical' procedures achieve the resurfacing of the skin by removing unwanted skin by mechanical abrasion. Microdermabrasion is a light, non-invasive non-surgical cosmetic procedure that works to achieve the removal of dead skin cells in the topmost layer of the epidermis by action small abrasive granular crystals of, for example, aluminium oxide. Microdermabrasion is useful for cosmetically treating fine irregularities in the texture of the skin, fine wrinkles and superficial scarring, but it is temporary in its effect and it is typically not capable of improving the appearance of the skin by deep resurfacing and rejuvenation to remove more significant wrinkles and scarring.

Dermabrasion, on the other hand, is a more significant, surgical procedure for effectively removing the top to mid-layers of the skin (the epidermis and even the dermis) using abrasive wheels, brushes and sandpaper to mechanically attack and remove unwanted skin. As deep layers of skin tissue are removed, significant bleeding can often result and so a local or even general anesthetic is required and dermabrasion is typically performed by a medical professional in a medical or surgical setting. The deep ablation and resurfacing of skin by dermabrasion can, following recovery, achieve an improved skin appearance by removing deeper scarring, fine wrinkles and skin irregularities. However, with dermabrasion there is no fine depth control, and the abrasives have to be applied to a wide area of the skin in order to 'blend' the finish, preventing effective treatment of localized irregularities. The traumatic effect on the skin and required recovery time of dermabrasion is significant.

Chemical peel procedures use a variety of chemical types which when applied directly to the skin, change the skin composition and cause unwanted skin to slough off the surface. Lighter peels can be applied in non-medical settings in cosmetic skincare treatment centres and these can achieve moderate, longer term improvement in the appearance of fine wrinkles and minor skin irregularities. However, medium and higher strength peels that remove skin to deeper layers are surgical treatments that require the expertise of medical practitioners to understand the effect of the chemical peel mixture, but can achieve improved skin appearance of more significant wrinkles and irregularities. However, there is no fine depth control available in any chemical peels, and the peel treatment must be applied to the whole area of the skin—e.g. the face, preventing localized treatment. Chemical peels can often require long recovery periods and also side effects on the skin such as photosensitivity. Repeat peels may also be needed to achieve a desired effect for a longer term.

Laser skin resurfacing, however, has addressed a number of shortcomings of dermabrasion and chemical peels and is capable of achieving skin resurfacing and rejuvenation to significantly improve skin appearance, and can even reduce the appearance of deeper wrinkles including frown lines and crows feet. Here, a $CO_2$ or Er:YAG laser light is used to act to rejuvenate the skin by dissociating the molecular bonds in the surface and subsurface layers of the skin to induce trauma and cause the skin (in particular the layers of the epidermis) to rejuvenate. In addition, the deep heating of the lower layers of the skin by the laser is understood to stimulate fibroblasts in the dermis to form new collagen and elastin to increase the turgor (elasticity) and thickness of the skin, helping to reduce the appearance of deep wrinkles and aging skin. Rather than laser treating the entire surface of the skin, laser treatments typically are delivered to a fraction of the skin in a pattern of pinpoints (or Microscopic Treatment Zones, MTZ) spread over an area of the skin, between which healthy skin remains, which reduces healing time and recovery. Compared to dermabrasion and chemical peels, laser treatment does allow a degree of localized control based on the requirements of the skin area by area. However, this pinpoint patterning of the ablated skin can leave a visible patterned finish even after recovery that is emphasized should further treatment (such as a facelift) be undertaken. As a result of this finish, laser skin resurfacing is not suitable for using in treating small 'zones' of skin, as the pattern of pin pricks cannot be blended.

A metric useful for assessing energy sources for ablation is fluence, defined for pulsed laser ablation energy sources as the energy of the laser pulse (Joules, J) divided by the area of the incident laser spot (in $cm^2$). Generally, the greater the fluence of the laser, the greater the depth of penetration and rejuvenation of the dermis. For a typical comparison, energy levels achieved using one, well-known system marketed under the trade name Fraxel™ re:pair™ available from Fraxel range from 5-70 mJ/MTZ, giving a high level of equivalent fluence in the order of a hundred Joules per $cm^2$. Thus a high, concentrated energy transfer is achievable with pulsed fractionated laser systems to a low level of the dermis. For the Fraxel™ re:pair™ system, the penetration depth achievable is from 200-1500 microns. As such, laser treatment is capable of achieving improved deep wrinkle reduction and skin resurfacing with significantly reduced bleeding, side effects and recovery time compared to dermabrasion and strong chemical peels. As a result, laser skin resurfacing can be provided as a cosmetic non-surgical treatment in a non-medicalised setting, administered by a trained operator who is not necessarily a medical professional.

It has been suggested that plasma, the fourth state of matter, formed by, for example, ionizing a gas, could be used to rejuvenate skin. One such system using a gas plasma for ablative tissue rejuvenation was developed by Rhytec Ltd in the United Kingdom and is now marketed under the brand name of NeoGen™ by Energist Ltd. of United Kingdom, for which more information is currently available from the following URL: http://www.energistgroup.com/.

Rhytec Ltd's International patent application publication no. WO 2001/62169 A2 discloses the technology underlying the development of the NeoGen™ system. The Rhytec Ltd published patent application discloses a handheld surgical instrument having a conduit carrying nitrogen gas and an electrode structure and radio frequency pulsed power source arranged to produce a dielectric barrier discharge inside the conduit that weakly ionizes the nitrogen gas to produce a low energy, non-thermal plasma to be emitted at a nozzle of the conduit. The plasma produced at the nozzle is used in the cosmetic treatment of fine wrinkles and skin irregularities and operates to rapidly transfer heat to the dermis to stimulate collagen production and increase skin elasticity and thickness. However, unlike with laser treatments, this dermal heating and rejuvenation does not occur at the same time as direct ablation (e.g. by vapourisation) of the upper layers of the epidermis. Thus the side effects and down time of this treatment are less significant than for laser treatment. However, the energy levels transferrable by the NeoGen™ system are only 2-6 Joules per pulse across the size of the plasma plume, are relatively low and unconcentrated compared to laser skin resurfacing, being spread over a spot size of over a square centimetre, giving a low equivalent fluence value on the order of 1 $J/cm^2$. While, unlike for laser light, absorption of the plasma energy is not dependent on the presence of a particular cholorophore (e.g. water present in cells for $CO_2$ lasers) leading to more uniform absorption across cell types, skin types and structures, the low equivalent fluence of the NeoGen™ plasma system means that its ability to reliably and effectively treat deep wrinkles and achieve significant skin resurfacing is questionable. The lack of any direct skin ablation, combined with the low fluence, means that the usefulness of the NeoGen™ system for skin resurfacing and removal of significant skin irregularities and wrinkles is very limited. Indeed a large number of repeat procedures may be needed to achieve any noticeable benefit for anything more significant than fine wrinkles and minor skin imperfections.

Non-ablative treatments to improve the appearance of ageing skin include the use of dermal fillers, botox and collagen which are injected into the skin. However, these are invasive interventions that have significant side effects on the appearance of the individual by bulking out skin and paralyzing muscles. These treatments do not themselves fundamentally rejuvenate the skin, but rather they seek to achieve improved appearance by 'sculpting' the skin and 'filling out' wrinkles, which can appear unnatural.

Another non-ablative treatment is radio frequency, infrared or ultrasound skin tightening therapy in which radio frequency, infrared light or ultrasound waves are used to heat the skin to attempt to promote collagen formation to tighten the skin. However, the effect of these treatments is not significant and is only short term in benefit, requiring a large number of repeat sessions.

In view of the above, there is an interest in new treatments for promoting skin rejuvenation and reducing the appearance of wrinkles and skin irregularities. In addition, the ablation and trauma principle is also used for other surgical purposes, notably wound debridement and tissue regeneration.

It is in this context that the present invention is devised.

SUMMARY OF THE INVENTION

Viewed from one aspect, the present invention provides a method of generating a plasma plume from an open end of a plasma torch. The method comprises ionizing a feed gas using an arc discharge in a first cylindrical cavity in the plasma torch to produce a central thermal plasma emitted at an open end of the first cylindrical cavity. The method further comprises ionizing a feed gas using a dielectric barrier discharge in a second annular cylindrical cavity arranged around the first cylindrical cavity in the plasma torch to produce at an open end of the second annular cylindrical cavity a non-thermal plasma halo surrounding the central thermal plasma.

In accordance with the present invention, a high power plasma treatment is provided that has a wide range of utility. For example, a plasma procedure having the power to cosmetically treat deep wrinkles and significant skin irregularities is provided. The higher energy, two-stage plasma having a thermal central plasma blade and non-thermal plasma halo has a greater effect on patient outcomes than the prior art, low energy, non-thermal plasma-only devices. In addition, a low recovery period is achieved such that the procedure can be carried out by trained, non-medical personnel in a non-surgical setting. Indeed, cosmetic treatments may be carried out using the present invention in which no anaesthetic is required.

The two stages of the plasma may be operated incrementally such that the user may initiate only the halo non-thermal plasma to treat some areas of the skin at a lower energy level, whereas the central, thermal plasma may be selectively initiated in addition to the halo plasma to treat selected areas of the skin at a higher energy level. In this way, the energy range achievable, and range of utility of the device, is extremely wide. Thus the plasma treatment system can be used to treat deep wrinkles and significant skin irregularities in a similar way to fractionated laser treatments (albeit with fewer side effects and on a more zonal basis as blending is easier), and also used to treat other areas of the skin for fine lines and wrinkles at lower energy levels.

The fluence achievable with the two stage plasma is in the region of 10-100 $J/cm^2$, which is comparable to the Fraxel™ laser systems, whereas the fluence achievable using only the halo non-thermal plasma is in the order of <1-10 $J/cm^2$, which is comparable to the NeoGen™ system.

While the high energy central thermal plasma is used to ablate tissue (e.g. layers of the epidermis, in a delayed fashion, to encourage rejuvenation and regeneration of the surface layers of the skin) and to thermally stimulate tissue (e.g. lower layers of the dermis to stimulate collagen formation), the non-thermal plasma halo has an effect of sterilizing the tissue surrounding the traumatized tissue, to facilitate healing thereof. In skin, the surface layer is ablated by the high energy plasma, but the surrounding tissue is sterilized by the halo and can remain in situ while the underlying and ablated layers heal such that a natural sterile dressing is formed by the plasma treatment itself, facilitating healing of the traumatized tissue. This further reduces recovery times for such a potentially deep wrinkle and rejuvenation treatment. Surface bleeding is in addition minimized, keeping down time low.

The arrangement of the two-stages of the plasma is such that they are caused to 'co-operate', whereby the highly ionized, energetic central thermal plasma "blade" produced by an arc discharge has a collimating effect on the surrounding non-thermal plasma halo, whereby at least some of the non-thermal plasma halo is entrained or focused by the central plasma. This brings the two types of plasma together into a more concentrated, co-operative plume in which an increased flux of free radicals, generated in the weak ionization of the gas by the dielectric barrier discharge in the non-thermal plasma, is produced at the energetic central tip of the plume. Entraining these free radicals in a high energy plasma blade tip causes the plasma plume to have an increased beneficial interaction with the tissue to promote rejuvenation and healing.

Thus, in embodiments, the method may further comprise: collimating and optionally entraining and/or focussing, using the central thermal plasma, at least some of the surrounding halo non-thermal plasma.

In addition, the plume shape enables the torch to be used in cosmetic treatments somewhat like a paintbrush, to treat local areas to a varying depth and effect, providing a flexible finish that is easily blended locally and so usable to treat small areas or zones, particularly deep wrinkle areas such as crow's feet or frown lines, without having to treat a wide area of the skin. This is unlike laser treatment, which is more like a sharp pencil, or leaves a finish like a dot matrix pattern if fractionated, and so cannot be blended easily nor used to treat small zones of the skin alone. Instead, with laser treatment, typically the whole of the face or at least a wide area thereof will need to be treated. The present invention allows targeted local treatment of deep wrinkles and other significant local skin irregularities.

In embodiments, the spot size and shape of the plume may be adjusted by, in embodiments, providing a plasma torch having an adjustable electrode geometry and adjusting the relative position thereof, increasing or decreasing the feed gas pressure, constricting or dilating the aperture of the open ends of the cavities, or increasing or decreasing or otherwise changing the power supply waveforms to the electrodes to generate the one or both of the two plasma stages. By providing an adjustable spot size and plume shape, the user can readily adapt the output plasma for different regions and conditions of the skin, like a palette of paintbrushes, allowing blending and bespoke treatments to be applied to small zones of the skin.

In embodiments, the method further comprises accelerating the thermal plasma towards a focal point in front of the open end of the torch. Focussing the plasma plume in this way gives a higher fluence and a greater effect on the tissue than a more dispersed, non-focussed plume.

In embodiments, the plasma torch comprises: a central cathode rod; a grounded conductive tube having an open end and being arranged around the cathode and spaced therefrom to form the first cylindrical cavity open at one end; and a high voltage electrode arranged around the grounded conductive tube and spaced apart therefrom to form the second annular cylindrical cavity, the high voltage electrode having a dielectric barrier material at a radially inward-facing surface thereof.

In embodiments, the method further comprises: producing the arc discharge in the first cavity between the cathode and grounded tube by providing to the cathode a constant direct current (DC) electrical power plus a high voltage pulsed electrical power to initiate the arc discharge; producing the dielectric barrier discharge in the second annular cylindrical cavity by providing to the high voltage electrode a high voltage alternating current electrical power or pulsed electrical power to generate the dielectric barrier discharge.

Viewed from another aspect, the present invention provides a method for the non-surgical cosmetic treatment of skin, comprising: generating a plasma in accordance with any of the methods of the present invention described herein, and directing the generated plasma plume at the skin requiring cosmetic treatment.

Viewed from another aspect, the present invention provides a method for the sterilization of objects in an industrial process, comprising: generating a plasma in accordance with any of the methods of the present invention described herein, and directing the generated plasma plume at the objects requiring sterilization. The sterilizing and heating effects of the plasma generated by methods of the invention described herein has be found to have particular utility in the sterilization of objects, for example in industrial processes.

Viewed from one aspect, the present invention provides a plasma torch having an open end from which a plasma plume is emitted in use is disclosed. The plasma torch includes a central cathode rod, a grounded conductive tube having an open end and being arranged around the cathode and spaced therefrom to form a first cylindrical cavity open at one end; and a high voltage electrode having a dielectric barrier material at a radially inward-facing surface thereof and being arranged around the grounded conductive tube and spaced apart therefrom to form a second annular cylindrical cavity open at one end. In use, a constant direct current (DC) electrical power plus a high voltage pulsed electrical power is provided to the cathode producing an arc discharge in the first cavity between the cathode and grounded tube to generate a central thermal plasma emitted at an open end of the first cylindrical cavity. Also, in use, a high voltage alternating current electrical power or pulsed electrical power is provided to the high voltage electrode producing a dielectric barrier discharge in the second annular cylindrical cavity to generate a non-thermal plasma emitted from an open end of the second cavity as a halo around the central thermal plasma blade.

Thus, viewed from another aspect, the present invention provides a plasma torch having an open end from which a plasma plume is emitted in use, comprising: a central cathode rod; a grounded conductive tube having an open end and being arranged around the cathode and spaced therefrom to form a first cylindrical cavity open at one end in which, in use, an arc discharge between the cathode and grounded tube ionizes a feed gas to produce a central thermal plasma emitted from the open end of the first cavity; and a high voltage electrode having a dielectric barrier material at a radially inward-facing surface thereof and being arranged around the grounded conductive tube and spaced apart therefrom to form a second annular cylindrical cavity in which, in use, a dielectric barrier discharge between the high voltage electrode and grounded tube ionizes a feed gas to produce at the open end of the second cavity a non-thermal plasma halo surrounding the central thermal plasma. A plasma torch configured in this manner is thus able to produce, in use, a high energy two-stage co-operative plasma having particular utility in cosmetic and surgical treatments.

In embodiments, the plasma torch may be configured such that, in use, the spot size and shape of the plume may be adjustable by, in embodiments, providing a handpiece having an adjustable electrode geometry, enabling the feed gas pressure to be increased or decreased, providing one or more means for constricting or dilating the aperture of the open ends of the cavities, or providing a power supply unit operable in use to enable increasing or decreasing or otherwise changing the power supply waveforms to the electrodes to generate the one or both of the two plasma stages.

In embodiments, the end of the central cathode rod is recessed from an open end of the grounded tube such that, in use, the arc current causes a Lorentz force that accelerates the thermal plasma towards a focal point in front of the open end of the torch. The arrangement of the electrodes in this way causes a magnetic field generated in the first cavity by the current travelling through the grounded tube and the cathode (due to the arc discharge therebetween), with magnetic field lines flowing cylindrically around the cathode. This magnetic field itself has an effect on the charged thermal plasma generated by the arc discharge of producing a Lorentz force on the plasma, which, due to the recess of the cathode compared to the open end of the grounded tube, is directed towards the central common axis of the electrodes in front of the open end of the grounded tube. In this way, the thermal plasma is accelerated towards a focal point in front of the open end of the torch, allowing the plasma to be concentrated, giving a high fluence in the resulting plasma plume. In this respect, the acceleration of the plasma by a magnetic field induced by a current generated by the arc discharge creates a magnetohydrodynamic effect on the plasma, meaning that the accelerated plasma can be considered a magnetohydrodynamic plasma.

In embodiments, the relative axial extent of the cathode and grounded tube at the open end of the plasma torch is configured such that the resulting plasma plume is concentrated a given focal distance in front of the open end of the torch. In this way, the relative positioning and configuration of the electrodes is set to give a desired plume characteristic. In embodiments, the cathode and grounded tube are relatively axially moveable to allow a user of the torch to adjust a focal distance of the plasma plume. In this way, the relative positioning and configuration of the electrodes is adjustable to allow the operator to adjust the plume shape and intensity, to achieve a desired plume characteristic. This allows the operator a great degree of flexibility and control over the operation and effect of the plasma torch, and can be considered akin to providing the operator with a variety of paintbrushes with which to rejuvenate different areas of the skin.

In embodiments, the cathode, grounded tube and high voltage electrode are arranged co-axially.

In embodiments, the plasma torch further comprises an annular permanent magnet arranged radially outwardly of the grounded tube at the open end thereof and configured to produce a magnetic torque on the arc discharge to cause the arc discharge, in use, to rotate around the cathode. The provision of the annular permanent magnet causes the high energy arc to rotate around the cathode, which allows the heat generated in the cathode and grounded tube at the arc location time to be dissipated. This can extends the lifetime of the 'hot' electrodes as, if the arc were repeatedly incident at the same location on the cathode and grounded tube, these electrodes could overheat and wear out relatively quickly. In accordance with this embodiment, the lifetime of the electrodes is extended, reducing maintenance, and improving the practicality of the two-stage plasma generation system. In other embodiments, however, the permanent magnet can be omitted completely.

In embodiments, at least the cathode, grounded tube and high voltage electrode are arranged such that, in use, the central thermal plasma collimates, and optionally entrains and/or focusses, at least some of the surrounding halo non-thermal plasma.

In embodiments, the plasma torch is configured as a handpiece for an end user to hold and manipulate in use. The handpiece may be provided with one or more controls to ignite the outer, non-thermal plasma and also, in addition, the central, thermal plasma.

In embodiments, the plasma torch further comprises an ergonomic grip coupled to the handpiece to facilitate user operation. In embodiments, the plasma touch comprises interchangeable ergonomic grips detachably coupleable to the handpiece. The interchangeable ergonomic grips may include one or more of: a trigger grip; a tripod grip; a pen grip. By providing the plasma torch as a handheld tool, having ergonomic and selectable grips aids the user in manipulating the plasma plume and allows fine control and comfort in use.

In embodiments, the cathode is detachably connected to the torch as a or as part of a replaceable modular assembly. Alternatively, or in addition, the high voltage electrode is detachably connected to the torch as a or as part of a replaceable modular assembly. In embodiments, the cathode and high voltage electrode are separately detachably connected to the torch as parts of separately replaceable modular assemblies. In embodiments, the grounded tube and cathode are together detachably connected to the torch as parts of a replaceable modular assemblies. In embodiments, the plasma torch and each modular assembly have mutually cooperating screw threads to enable the detachable connections therebetween. By providing the plasma torch with a modular construction having readily changeable modular parts for the 'hot' electrode section (including the cathode) and/or the 'cold' electrode section (including the high voltage electrode), if and when the electrodes become worn, they are readily replaceable without the need for disassembly of the torch by a service engineer. Instead, the worn electrode modular components can be removed by the end user, for example by unscrewing them from the torch, and replaced with new or reconditioned modular components.

Viewed from another aspect, the present invention provides a modular cathode assembly in a plasma torch in accordance with the aspects and embodiments of the invention described herein, the modular cathode assembly comprising a cathode and optionally a grounded tube and being configured to be detachably connectable to the plasma torch to enable the cathode thereof to be replaced.

Viewed from another aspect, the present invention provides a modular high voltage electrode assembly in a plasma torch in accordance with the aspects and embodiments of the invention described herein, the modular high voltage electrode assembly comprising a high voltage electrode and being configured to be detachably connectable to the plasma torch to enable the high voltage electrode thereof to be replaced.

In embodiments, the plasma torch further comprises: at least one feed gas inlet opening for each of the first and second cavities; wherein the plasma torch is configured to provide sealed fluid communication between each feed gas inlet and a feed gas connector for connecting to a feed gas supply. In embodiments, separate feed gas connectors are provided for each of the first and second cavities, and wherein the plasma torch is further configured such that fluid communication lines between the feed gas connectors and the feed gas inlets to the first and second cavities are sealed from each other, such that separate feed gases are in use supplied to the first and second cavities.

Viewed from another aspect, the present invention provides an electrical power generator unit coupled with and providing power in use for a plasma torch in accordance with the aspects and embodiments of the invention described above, the electrical power generator unit comprising: means configured to provide to the cathode in use a constant direct current (DC) electrical power supply plus a high voltage pulsed electrical power supply to initiate the arc discharge in the first cylindrical cavity (the thermal plasma power supply); means configured to provide to the high voltage electrode in use a high voltage alternating current electrical power supply or pulsed electrical power supply to generate the dielectric barrier discharge in the second annular cylindrical cavity (the non-thermal plasma power supply).

The thermal and non-thermal power supplies may be operated independently, for example in response to user control, such that the two stages of the plasma may be operated incrementally so that, in use, the user may initiate only the halo non-thermal plasma to treat some areas of the skin at a lower energy level, whereas the central, thermal plasma may be selectively initiated in addition to the halo plasma to treat selected areas of the skin at a higher energy level.

Viewed from another aspect, the present invention provides an apparatus for generating a plasma plume, comprising: a plasma torch in accordance with the aspects and embodiments of the invention described herein; and an electrical power generator unit in accordance with the aspects and embodiments of the invention described herein.

In embodiments, the apparatus further comprises one or more containers of feed gas connected to the plasma torch, wherein the apparatus is configured such that feed gas is supplied to the first and second cavities to be ionized in use.

Viewed from another aspect, the present invention provides a method of generating a plasma plume using apparatus for generating a plasma plume torch in accordance with the aspects and embodiments of the invention described herein, the method comprising: providing to the cathode using the electrical power generator unit a constant direct current (DC) electrical power plus a high voltage pulsed electrical power to initiate the arc discharge in the first cylindrical cavity between the cathode and grounded tube to thereby ionize a feed gas supplied thereto to produce a central thermal plasma emitted from the open end of the first cylindrical cavity; and providing to the high voltage electrode using the electrical power generator unit a high voltage alternating current electrical power or pulsed electrical power to generate the dielectric barrier discharge in the second annular cylindrical cavity between the high voltage electrode and the grounded tube to thereby ionizes a feed gas supplied thereto to produce at the open end of the second cavity a non-thermal plasma halo surrounding the central thermal plasma.

A control module configured in use to cause the apparatus to perform the above method may be provided as part of the apparatus. The control module may be implemented using hardware or hardware and software. There may be provided a data processing module and computer readable medium, optionally non-transitory, comprising instructions which when carried out by the data processing module configure the apparatus to implement the control module.

Viewed from another aspect, the present invention provides use of a plasma torch or an apparatus in accordance with the aspects and embodiments of the invention described herein in the non-surgical cosmetic treatment of skin, optionally for one or more of: wrinkle removal; skin resurfacing; skin ablation; scar removal; hair removal.

Viewed from another aspect, the present invention provides use of a plasma torch or an apparatus in accordance with the aspects and embodiments of the invention described herein in non-surgical treatment.

Viewed from another aspect, the present invention provides use of a plasma torch or an apparatus in accordance with the aspects and embodiments of the invention described herein in surgical treatment of live tissue, optionally for one or more of: cauterization; tissue ablation for wound healing; wound or burn sterilization; cavity sterilization.

Viewed from another aspect, the present invention provides use of a plasma torch or an apparatus in accordance with the aspects and embodiments of the invention described herein in an industrial sterilization process, optionally for sterilizing one or more of: foodstuffs; pharmaceuticals; medical implants; medical instruments; surfaces and industrial components.

BRIEF DESCRIPTION OF THE DRAWINGS

Aspects of the invention may best be understood by reference to the following description of certain exemplary embodiments together with the accompanying drawings in which.

DETAILED DESCRIPTION OF PREFERRED EMBODIMENTS

The detailed description set forth below in connection with the appended drawings is intended as a description of presently preferred embodiments of the invention, and is not intended to represent the only forms in which the present invention may be practised. It is to be understood that the same or equivalent functions may be accomplished by different embodiments that are intended to be encompassed within the spirit and scope of the invention. Furthermore, terms "comprises," "comprising," or any other variation thereof, are intended to cover a non-exclusive inclusion, such that apparatuses and method steps that comprises a list of elements or steps does not include only those elements but may include other elements or steps not expressly listed or inherent. An element or step proceeded by "comprises . . . a" does not, without more constraints, preclude the existence of additional identical elements or steps that comprises the element or step.

Figure 1:
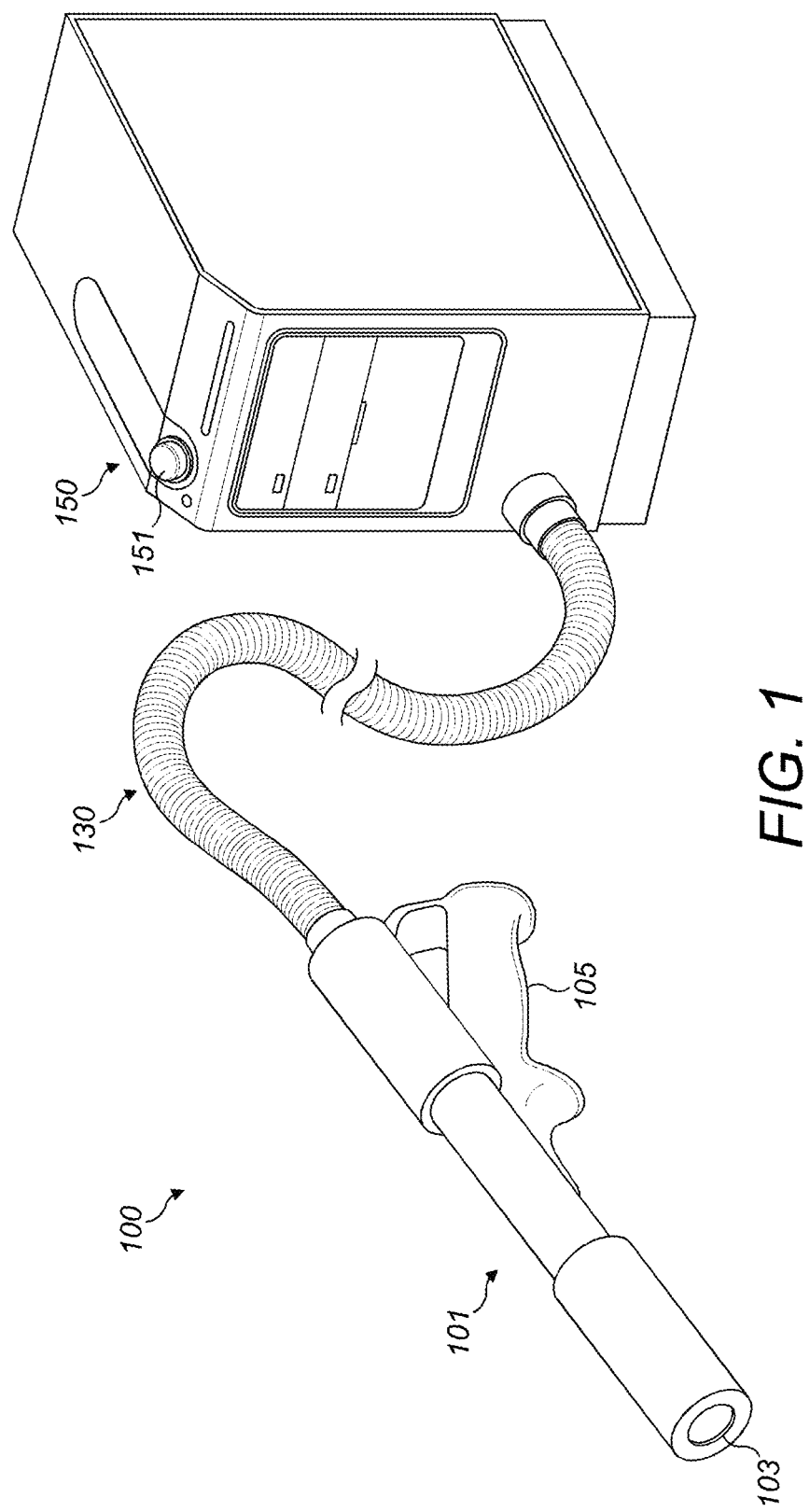
FIG. 1 shows a view of an apparatus for generating a plasma plume for cosmetic treatment of skin according to an embodiment of aspects of the invention.
Figure 2:
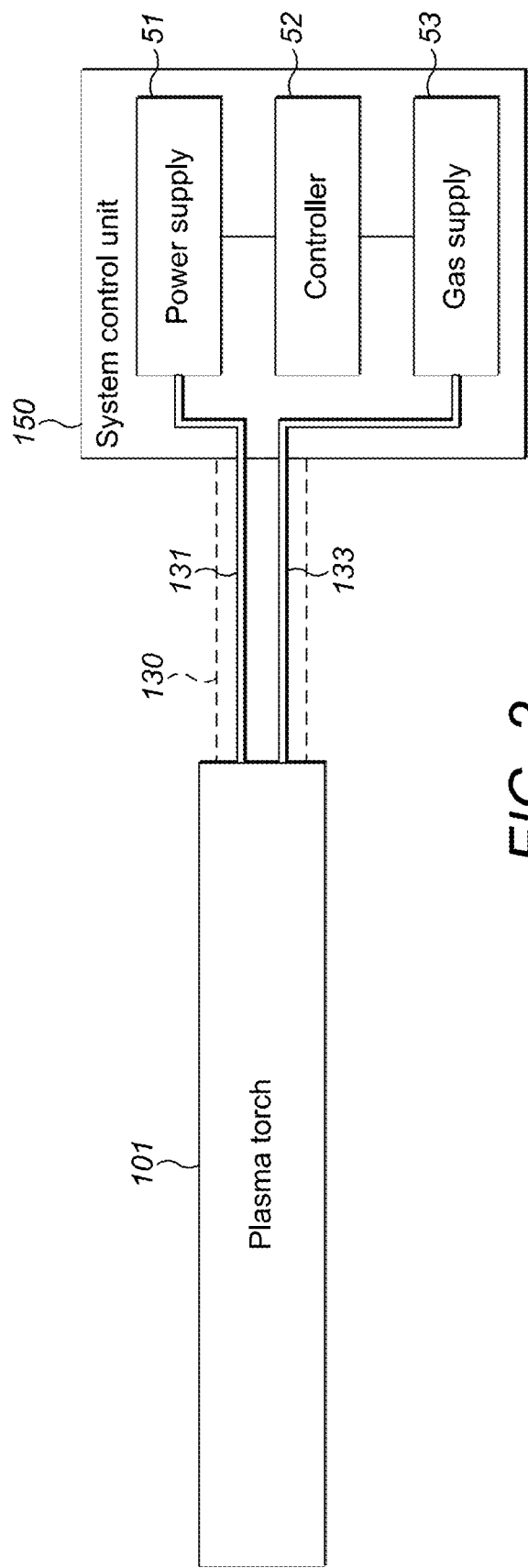
FIG. 2 is a schematic drawing illustrating the apparatus shown in FIG. 1 showing components of the system control unit.

Referring now to FIGS. 1 and 2, an apparatus 100 for generating a plasma plume in accordance with an embodiment of aspects of the invention includes a plasma torch 101 connected via a connector hose 130 to a system control unit 150. As will be explained in further detail below, by operating the system control unit 150 by means of controls 151, the controller 52 of the system control unit 150 can be caused to release one or more feed gases from gas supply 53 where they are stored under pressure to ionization cavities inside the plasma torch 101. Once the gas is flowing to the plasma torch 101 through gas supply conduit 133 provided in the hose 130, the controller 52 causes the power supply to generate one or more different electrical power signals that are provided via power supply cabling 131 provided in the hose 130 to one or more electrodes in the plasma torch 101 to cause electrical discharge inside the plasma torch 101. The feed gas inside the plasma torch is then ionised by the discharge and is emitted from the open end 103 of the plasma torch 101 in the form of a two-stage plasma plume, as described in more detail below. The plasma plume may be generated for a sustained period of time or may be caused to be emitted in pulses.

The operator of the apparatus 100 can, by holding the plasma torch by way of ergonomic grip 105, manipulate the plasma torch to direct the plasma plume emitted from opening 103 onto tissue to carry out cosmetic or surgical procedures. To allow easy user control, the plasma torch 101 may be provided with one or more controls (not shown) such as trigger buttons on grip 105 to ignite the outer, non-thermal plasma and also, in addition, the central, thermal plasma. For example, the plume may be used for the cosmetic treatment of deep wrinkles such as crow's feet and other, significant skin irregularities. The ergonomic grip 105 shown in FIG. 1 is a trigger grip, but this is removably attached to the plasma torch 101 such that it can be changed for other ergonomic grips which may be specifically adapted for a given operator's hand. This allows the operator a high degree of comfort and accuracy when holding the plasma torch 101 for extended periods in use.

The plasma generated by the apparatus 100 is a two-stage cooperative plasma having a higher energy central focused thermal plasma blade surrounded by a lower energy halo non-thermal plasma. Optionally, only the outer halo stage of the non-thermal plasma may be ignited.

Figure 3:
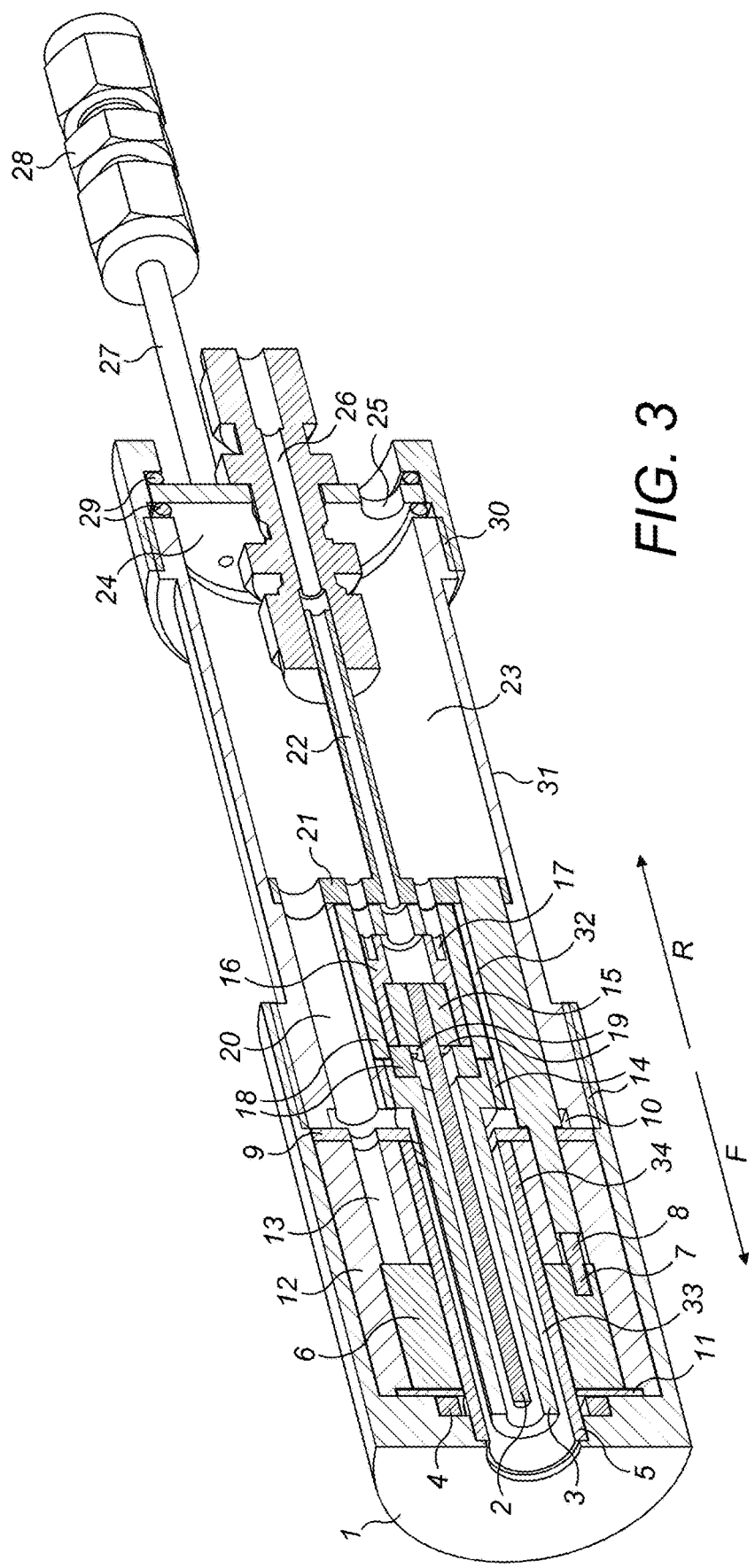
FIG. 3 is a cutaway view of a plasma torch according to an embodiment.

FIG. 3 is a cutaway view of the plasma torch 101 showing the electrode structure that gives rise to the creation of the two-stage cooperative plasma in use. The plasma torch 101 can be conceptually divided into two halves. The front half, indicated by the arrow F in FIG. 1, contains the electrodes and cavities to which gas is fed for ionisation and from which the two-stage plasma is emitted in use. The front half of the plasma torch 101 is constructed by two user-replaceable modular components, facilitating servicing of the plasma torch 101 when the electrodes therein become worn. The rear half of the plasma torch 101, indicated by the arrow R in FIG. 1, acts to support and retain the components of the front half and to provide a coupling to the hose 130 to enable sealed fluid communication of the gas supply from the gas supply conduit 131 of the hose 130 to the cavities 33, 34 in the front half—and to electrically couple the electrodes 2, 6 in the front half F to the electrical power cabling 131 of the hose 130.

The components of the plasma torch 101 in the front half F are encased in a grounded stainless steel casing 1. The casing 1 is tubular in form having at its front end an end wall with an axially centralised opening 103 for admitting the plasma plume in use. The back end of the casing 1 has a screw thread 14 provided on a radially inward-facing surface thereof that mutually cooperates with and is retained by a corresponding screw thread 14 provided on a radially outward facing surface of a front end of a grounded stainless steel body 31 forming the rear end R of plasma torch 101. A threaded sleeve (not shown) rotatable relative to the casing 1 may be provided on the casing 1 for threading onto the thread 14 of the stainless steel body 31 to allow the front F and rear R parts of the torch to be mated without relative rotation. The body 31 has towards its front end a solid block machined into a perforated bulkhead 32, described in more detail below, that acts to retain certain other components of the plasma torch 101 and to admit feed gas and electrical coupling wires from the rear to the front of the plasma torch 101.

A cathode rod 2, formed of either tungsten or thoriated tungsten, is provided in the front half of the plasma torch 101 to extend along the central axis thereof. Arranged coaxially around the cathode rod 2 and spaced apart therefrom, there is provided a grounded stainless steel arc tube 3. A cylindrical annular cavity 33 formed between the rod 2 and the grounded tube 3 is open at its front end but it is sealed at its back end, except for feed gas inlets. As will be explained in greater detail below, in use, the cathode rod 2 is provided with an electrical power signal sufficient to create an arc between the cathode rod 2 and the grounded tube 3 which is used to generate a 'hot' thermal plasma in the cylindrical annular cavity 33 that is then emitted from the open front end of the cavity 33. It should be noted that the axial extent of the cathode rod 2 at the front end thereof is slightly recessed relative to the open end of the front of the grounded tube 3. This relative positioning causes a Lorentz force to be generated by the current of the arc discharge which causes the charged particles of the central thermal plasma to be accelerated towards the central axis of the plasma torch 101 causing the hot stage of the plasma plume to become focused.

Arranged radially outside the grounded tube 3 at its front end is an annular NdFeB permanent magnet 4 that creates a magnetic field that provides a stabilising magnetic torque on the arc between the cathode 2 and grounded tube 3 and causes the arc to rotate around the cathode 2 in use. This prevents the arc from being sustained at a single location between the cathode rod 2 and grounded tube 3 which may prevent the cathode 2 from overheating and becoming damaged. This can extend the life of the components of the plasma torch 101 and the conservation of the cathode 2 by the magnet 4 allows the use of an arc discharge to become more practical. In alternative embodiments, however, the permanent magnet may be omitted.

Arranged coaxially around the grounded tube 3 and spaced apart therefrom is a Borosilicate glass or ceramic (Boron Nitride/Alumina) tube 5 that has a dielectric constant of 4.6 and that acts as a dielectric barrier to a high-voltage copper electrode 6 arranged radially outwardly thereof. A second cylindrical cavity 34 is formed between the grounded tube 3 and the dielectric barrier tube 5 that is open at its front end but is sealed at its back end by bulkhead 32, except for inlets formed by bores 20 in the bulkhead 32 that enable the passage of feed gas, a thermocouple 13 and a coaxial power supply cable 8 from the rear R to the front F of the plasma torch 101. As will be explained in greater detail below, in use, the high-voltage electrode 6 is provided with an electrical power signal sufficient to create a dielectric barrier discharge between the dielectric barrier tube 5 and the grounded tube 3 which is used to generate a 'cold' non-thermal plasma in the cylindrical annular cavity 34 that is then emitted from the open front end of the cavity 34.

The high-voltage electrode 6 is connected to a brass threaded rod 7 acting as high voltage connector and having a conductive core of a coaxial cable 8 soldered to it. In use, the coaxial cable 8 conducts the high-voltage electric power signal generated by the power supply 51 via the electrical power cabling 131 to the high-voltage electrode 6.

A grounded brass plate 9 is provided in the front part of the plasma torch 101 surrounding the grounded tube 3 in front of the bulkhead 32 but slightly spaced therefrom. The grounded shielding 10 of the coaxial cable 8 is soldered to the brass plate 9 to provide the ground reference. The brass plate 9 is in contact in contact with the casing 1 and body 31 and acts as the ground reference for the grounded components of the plasma torch 101.

A ceramic (Boron Nitride/Alumina) disc 11 is arranged between the magnet 4 and the high-voltage electrode 6 to electrically and thermally insulate them from each other. A further ceramic (Boron Nitride/Alumina) block 12 is arranged to extend around the high-voltage electrode 6 to electrically and thermally insulate the high-voltage electrode 6 from all other grounded metal surfaces. A bore 13 is formed in the block 12 to receive a thermocouple (not shown) arranged to monitor temperature of the high-voltage electrode 6 in use to ensure that it does not overheat. A further bore is formed on the block 12 to receive the coaxial cable core 8 for connection to the high-voltage electrode 6 via the high-voltage connector 7. Holes are provided through the brass plate 9 and the bulkhead 32 registered to the bores provided in the block 12 for passing the thermocouple and coaxial cable from the rear to the front of the plasma torch 101.

The bulkhead 32 is also perforated centrally by a large central bore that contains a brass cathode connector 16 surrounded by ceramic (Boron Nitride/Alumina) components 18 provided radially outwardly and to the rear of the cathode connector 16 to electrically and thermally insulate the cathode connector 16 from all other grounded metal surfaces. A bore in the brass cathode connector 16 forms a cavity sized to receive a stainless steel cathode base 15 with an interference fit therein. The cathode 2 is supported by and extends from the cathode base 15 to the front of the plasma torch 101. A ceramic insulator 18 to the front of the cathode connector 16 insulates the cathode 2, cathode base 15 and cathode connector 16 from the grounded steel tube 3.

The grounded tube 3 has an enlarged cylindrical base having, on its radially outward facing surface a screw thread 14 that mutually co-operates with a screw thread 14 provided on a radially inner surface of the central bore of the bulkhead 32, such that the grounded tube 3 is releasably engageable with the grounded steel body 31 and is grounded thereby in use.

In the embodiment, a replaceable "cold tip" module is provided by the grounded casing 1 and contains the permanent magnet 4, dielectric tube 5, ceramic insulators 11, 13 and brass plate 9. These components are provided together in a single assembly that is releasably engageable with the steel body 31 of the rear of the plasma torch 101 by means of screw thread 14 provided on the radially outer surface of the steel body 31.

In the embodiment, a replaceable "hot tip" module is provided by the cathode 2, grounded tube 3, cathode base 15 and the ceramic insulator component 18 sandwiched between the cathode base 15 and the enlarged cylindrical base of grounded tube 3. These components are provided together in a single assembly that is releasably engageable with the steel body 31 of the rear of the plasma torch 101 by means of screw thread provided on the radially inner surface of the bulkhead 32 of the steel body 31. The interference fit between the cathode base 15 and the cathode connector 16 form a mateable and the demateable male-female connector, in which the cathode base 15 forms the male part then the cathode connector 16 forms the female part.

The cold tip and hot tip modules can be easily replaced by the user to service the plasma torch 101 when the electrodes thereof become worn. In other embodiments, the cold tip, which includes the high-voltage electrode at least, and the hot tip, which includes the cathode at least, may be constructed differently and have different components in the assembly to that shown for the embodiment described in detail in FIG. 3. For example, a fastening mechanism other than a screw thread may be usable to connect the hot tip and cold tip modules to the body of the plasma torch 101.

To the rear of the bulkhead 32, the wall of the body 31 of the plasma torch 101 forms a cylindrical chamber 23 closed at the rear end by an end cap 30 having a radially extending feed through plate 24 having holes there through and connectors for interfacing with the power supply 51 and gas supply 53 via the gas supply conduit 133. The end cap 30 is joined to the body 31 by means of a screw thread.

Abutting against the rear facing surface of the bulkhead 32, a stainless steel retainer plate 21 retains the cathode connection assembly 16 in place by being screwed into the rear facing ceramic insulators 18 and bulkhead 32. Extending from the axial centre of the retainer plate 21 is an integral stainless steel spindle 22 having a bore extending centrally there through open at both ends. The rear of the spindle 22 is joined to a swage lock connector 26 that penetrates through feed through plate 24 that closes off and seals the chamber 23 formed by cylindrical body 31. In use, the feed gas supply for the central, thermal plasma to be ionised in the hot tip is connected to the swage lock connector 26. A fluid communication channel is thereby provided between the swage lock connector 26 and the cavity 33 via the central bore of the spindle 22, through holes penetrated through the centre of the ceramic insulator 18 provided at the rear end of the cathode connector 16 through the cathode connector 16 itself, and also through grooves provided through the stainless steel cathode base 15 that allow the feed gas to pass around the interference fit between the cathode base 15 and cathode connector 16 and through into the cavity 33 formed in the space between the cathode rod 2 and the grounded tube 3.

A second swage lock connector 28 is connected to the feed through plate 24 and provides a fluid communication channel into the chamber 23 formed inside the rear of the body 31 closed by the feed through plate 24. In use, the cold feed gas supply is connected to the swage lock 28 such that the chamber 23 in the rear of the body 31 is filled with cold feed gas. Nitrile O-rings 29 arranged between the feed through plate 24 and the body 31 to provide a seal between the external atmosphere and the interior of the device when under compression. Four bores 20 provided extending through the retainer 21 and bulkhead 32 provide fluid communication paths for the cold feed gas from the chamber 23 at the rear R of the plasma torch 101 to the front of the plasma torch 101. A radially extending gap formed between the front F of the bulkhead 32 and the brass plate 9 allows cold plasma feed gas from the bores 20 to pass into the cavity 34 in which the cold plasma is formed in use by an annular gap between the brass plate 9 and the grounded tube 3.

One of the bores 20 performs the alternative function of providing a passageway for the high-voltage coaxial cable 8 that extends from a hole in the feed through plate 24 at the rear of the plasma torch 101, through the cold plasma chamber 23, through a hole in the retainer plate 21, through the bore 20 in the bulkhead 32, through a hole in the brass plate 9, and through a bore in the ceramic insulator 12. At the front of the bore in the ceramic insulator 12 the conductive core of the coaxial cable 8 is connected to the high-voltage electrode 6 by a high-voltage connector 7. In this way, a conductive connection is formed between from the high-voltage electrode 6 and power supply 51 via electrical power cabling 131.

To connect the power supply 51 to the cathode 2, holes are provided in the retainer 21, ceramic insulator 18 to the rear of the cathode connector 16 opening into bores in the cathode connector 16 itself. Single core wires extending into the plasma torch via holes in the feed through plate 24 extend through the chamber 23 and through the holes in the retainer 21 and ceramic insulator 18 whereby the wire core is soldered to the cathode connector 16. In this way, a conductive connection is formed between the cathode 2 and power supply 51 via electrical power cabling 131.

In the embodiment shown in FIG. 3, the first cavity 33 and second cavity 34 are sealed from each other such that they are not in fluid communication (except via the open front ends) and separate gas supplies are connected through the hose 130 to feed the first 33 and second 34 cavities separately. Noble gases such as nitrogen or argon or mixtures thereof may be used as feed gases and different types or compositions of these gases may be fed separately to the first 33 and second 34 cavities. Alternatively, the same type or composition of gases may be fed separately to both the first 33 and second 34 cavities. Alternatively, in other embodiments, the fluid passages for communicating feed gas from the rear R to the front F of the plasma torch 101 may be unified/in fluid communication such that a single gas supply may be used to feed gas of the same type to the first 33 and second 34 cavities.

Operation of the apparatus 100 to generate the two-stage cooperative plasma plume will now be described with reference to FIGS. 2, 4 and 5.

In order to begin production of the two-stage plasma, the gas supply 51 in the system control unit 150 is caused by the controller 52 in response to user operation of the controls 151 to begin releasing feed gas under pressure to the first 33 and second 34 cavities via the gas supply conduit 133.

Then the controller 52 causes the power supply 51 to generate electrical power signals which are provided to the cathode 2 and high-voltage electrode 6 via the electrical power cabling 131.

Figure 4:
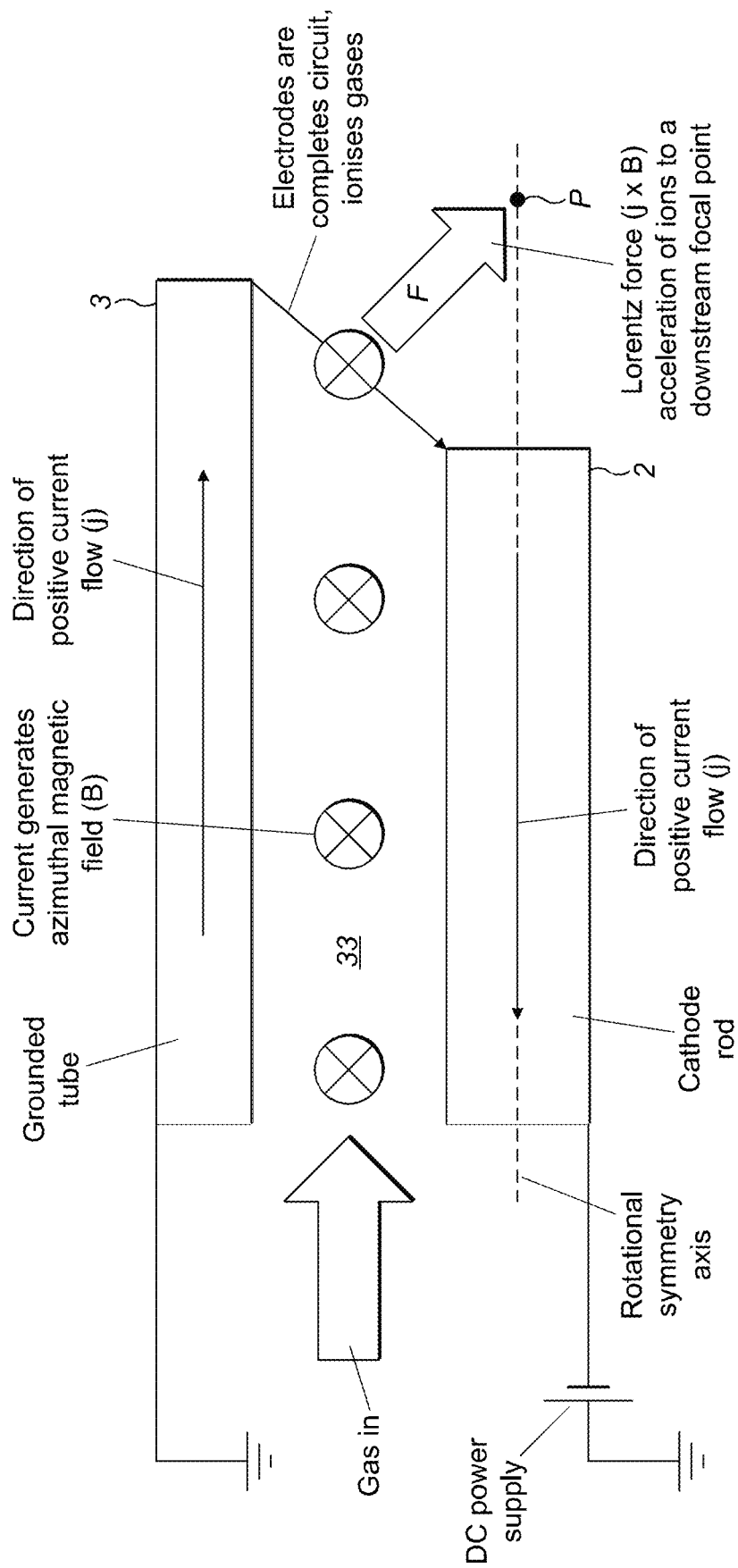
FIG. 4 is a diagram illustrating the operation of the 'hot' stage of the plasma torch shown in FIG. 3 to generate an arc discharge and thermal plasma.
Figure 6:
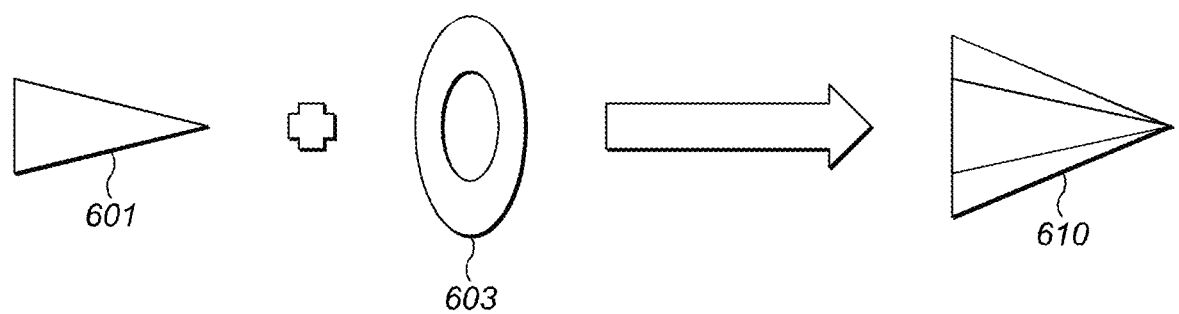
FIG. 6 illustrates the two stages of the plasma generated by the plasma torch and the cooperative effect to generate a collimated, focused plasma plume.
Figure 8:
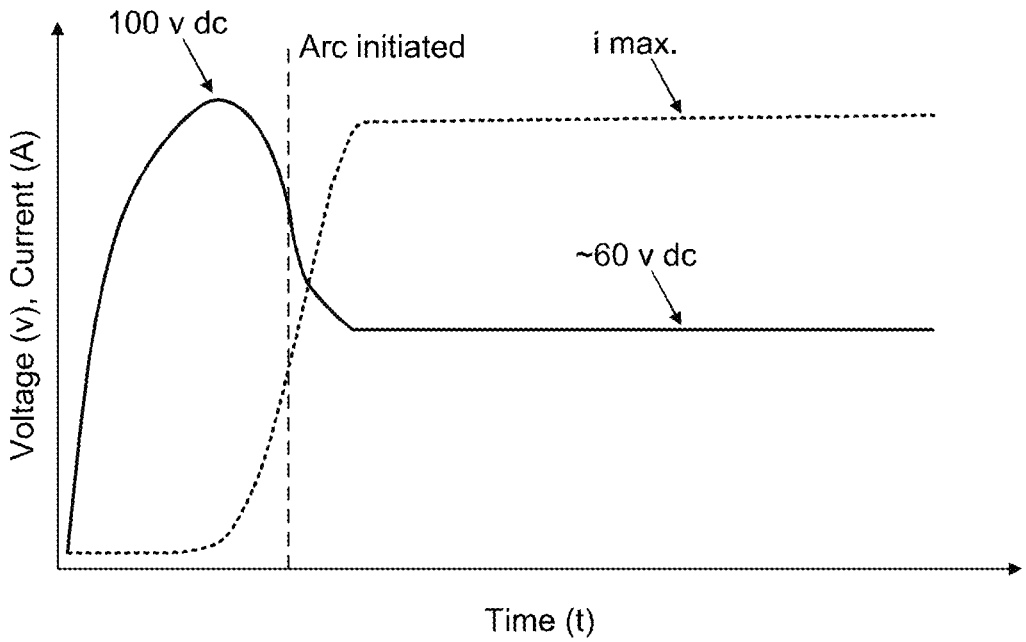
FIG. 8 shows a voltage and current vs time waveform generated by the DC power supply to generate the hot stage of the plasma (based on para[88])

As shown in FIG. 4, to generate the hot stage of the plasma, the cathode 2 is connected to a DC power supply provided by power supply 51. The DC power supply consists of a constant supply at ~25V, ~4.2 A DC plus a ballast/igniter high-voltage pulse circuit to initiate the arc discharge. This DC power supply generates and sustains a voltage and current vs time waveform as shown in FIG. 8 in which an initial voltage pulse of 100-200V is applied by the ballast/igniter circuit which, as the electrical field breaks down and an electrical arc is initiated between the cathode 2 and the grounded tube 3 through the feed gas then settles down to around 20-60V DC steady state. The electrical arc provides the heating and ionisation mechanism for generating from the feed gas the highly ionised, high-energy thermal plasma that provides the "hot" component of the device's plasma plume. The current j generated in the grounded tube 6 and cathode 2 by the sustained arc discharge has a current flow which can be varied between 2-6 A. This current flow causes the generation of an azimuthal magnetic field B around the cathode as illustrated in FIG. 4. As can be shown at the open end of the cavity 33, the interaction of this azimuthal magnetic field B and the electrical arc j generates a Lorentz force F that acts on the generated ions to accelerate the hot plasma in the direction shown by the arrow in FIG. 4 towards the axial centre of the plasma torch 101 to focus the thermal plasma towards a focal point P a distance in front of the open end of the cavity 33. In this way, the interaction of the plasma and the magnetic field B generates a magnetohydrodynamic (MHD) thermal plasma 'blade' 601 shaped as shown in FIG. 6. The high-energy of this highly ionised, focused thermal plasma produces a high fluence at the focal point which enables the apparatus 100 to have a significantly greater and more penetrative effect on the tissue, such as skin, to which it may be directed in use. As a result, the apparatus 100 achieves a significantly improved tissue resurfacing, regenerating and rejuvenating effect compared to known plasma tissue resurfacing devices, improving patient outcomes in both cosmetic and surgical tissue treatments. Indeed, the patient outcomes achieved by the apparatus 100 are comparable in order to the known laser systems, described above, without any of the attendant disadvantages like the pin-prick patterning on the skin. Instead, the finish on skin for cosmetic treatments using the two-stage plasma is smoother and more easily blended such that cosmetic treatment of smaller "zones" of the skin is enabled while still providing a homogeneous surface finish.

The magnetic torque produced by the magnet 4 on the arc causes the arc discharge to rotate around the cathode 2 minimising the heating damage and wear of the discharge on the cathode 2 and grounded tube 3, lengthening the operational lifetime of the "hot tip" components.

The plasma generation system 100 may be, in other embodiments, be configured such that, in use, the spot size and shape of the plume may be adjustable. While not shown in the embodiment of FIG. 3, a user-controllable electrode geometry alteration mechanism may be provided in the plasma torch to allow the operator to adjust the spot size and shape of the plume. For example, a mechanism may be provided to allow the user to adjust the relative axial positioning of the front ends of the cathode 2 and grounded tube 3 so as to adjust the directionality of the focusing Lorentz force that acts on the thermal plasma, and so also the focal distance, spot size, and spot energy/fluence of the resulting plasma plume. This may be manipulatable directly on the plasma torch, for example by means of a mechanical scroll wheel, or by means of controls 151. Alternatively, the electrode geometry may be adjusted by providing interchangeable electrode tips or other structural adaptations. Further controls may be provided in the plasma control system operable, for example, from control panel 151 which may allow the user to adjust the spot size or plume geometry by causing the feed gas pressure to be increased or decreased, providing one or more means for constricting or dilating the aperture of the open ends of the cavities, or providing a power supply unit operable in use to enable increasing or decreasing or otherwise changing the power supply waveforms to the electrodes to generate the one or both of the two plasma stages. Finely adjusting these parameters individually or in combination allows a variety of spot sizes and plume geometries to be achievable, allowing the plasma generation device to provide a palette of plasma plumes usable in a variety of different ways to facilitate treatment of different wrinkles and skin irregularities, and to facilitate blending. For example, a higher-energy, smaller size spot may be used to treat deep laughter line wrinkles formed around the mouth, whereas a lower-energy, larger size spot may be used to blend the treated laughter lines and to treat wider areas of fine wrinkles, such as crow's feet around the eyes.

Figure 5:
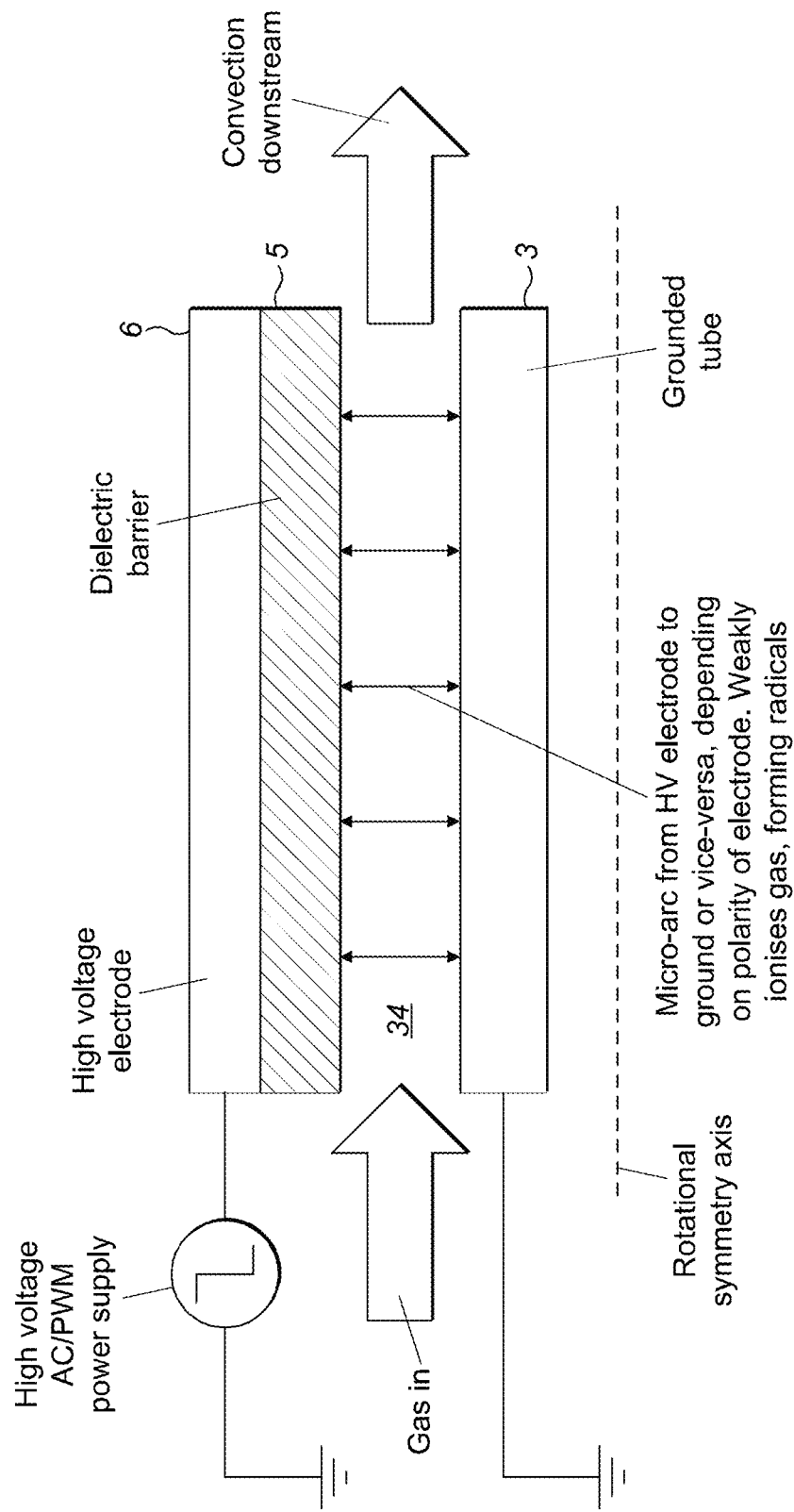
FIG. 5 is a diagram illustrating the operation of the 'cold' stage of the plasma torch shown in FIG. 3 to generate an dielectric barrier discharge and non-thermal plasma.
Figure 9:
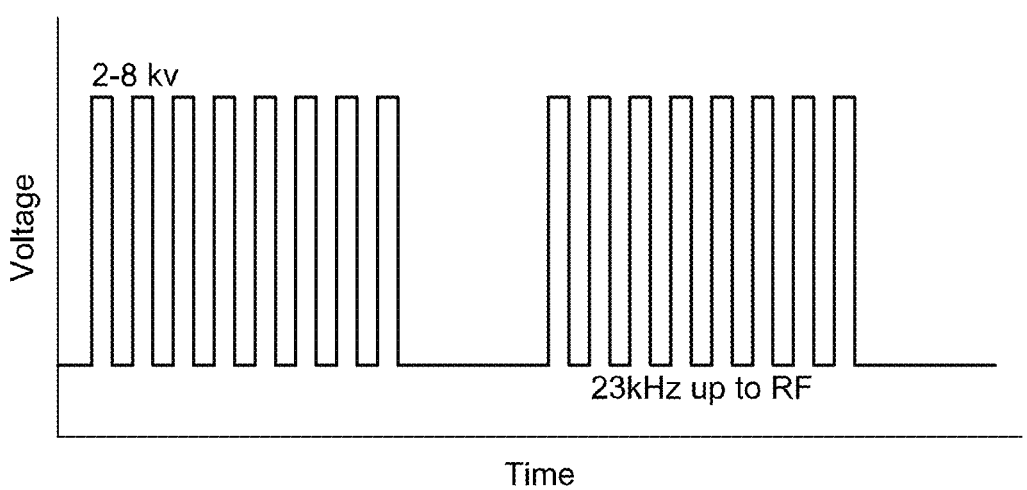
FIG. 9 shows a PWM voltage signal generated by the high voltage pulse width modulated power supply to generate the cold stage of the plasma (based on para[91]).

As shown in FIG. 5, to generate the cold stage of the plasma, the high-voltage electrode 6 is connected to a high-voltage pulse width modulated (PWM) power supply provided by power supply 51 (in other embodiments, an AC power supply may be used rather than a PWM, but a PWM is more efficient and effective in this context). The high-voltage PWM power supply consists of a variable frequency PWM power supply providing a PWM voltage signal to high voltage electrode 6 as shown in FIG. 9 of ~2-8 kV, ~25 mA at a frequency of 23 kHz up to RF for the duration of the cold stage discharge (two discharge pulses are shown in FIG. 9). This powers a dielectric barrier discharge between the grounded tube 3 and the dielectric barrier layer tube 5, providing the plasma production mechanism that weekly ionises the feed gas in cavity 34 that is convected downstream under pressure to provide an emission of annular, relatively low energy, non-thermal plasma as a cold stage shaped as a halo 603 surrounding the central high-energy, thermal plasma blade 601. The dielectric barrier discharge produces in the cold halo plasma a relatively high proportion of free radicals, which have a sterilising effect when incident on the tissue.

As shown in FIG. 6, the accelerated, high-energy MHD central thermal plasma blade 601 has a collimating and focusing effect on the surrounding convected relatively low energy dielectric barrier halo plasma 603 which, due to a shear induced turbulent flux from the thermal plasma blade 601, becomes entrained with the thermal plasma blade 601 to produce a cooperative, focused plasma plume 610. The plum 610 has a high-energy central plasma spot with a relatively high degree of free radicals that is used to ablate tissue and heat subsurface dermal layers. This is surrounded by an entrained sterilizing, relatively low energy, non-thermal plasma halo, which is the source of the free radicals, which acts to sterilise the trauma induced in the tissue in situ and to promote healing thereof.

When the cooperative plasma plume 610 is used to rejuvenate skin tissue and to treat deep wrinkles and other significant skin irregularities, the ablated surface layers of the tissue are not immediately vaporised and are instead caused to disintegrate and slough off over the course of a few hours to days. In the meantime, the heating and trauma caused to the subsurface epidermal and dermal layers that encourage collagen and elastin production and rejuvenation are sterilised by the plume and protected by the remaining surface epidermal layers such that the traumatised subsurface layers are provided with an in situ sterile dressing that significantly promotes healing and improves the recovery time while minimising the side-effects and downtime of the rejuvenating skin treatment.

Figure 7:
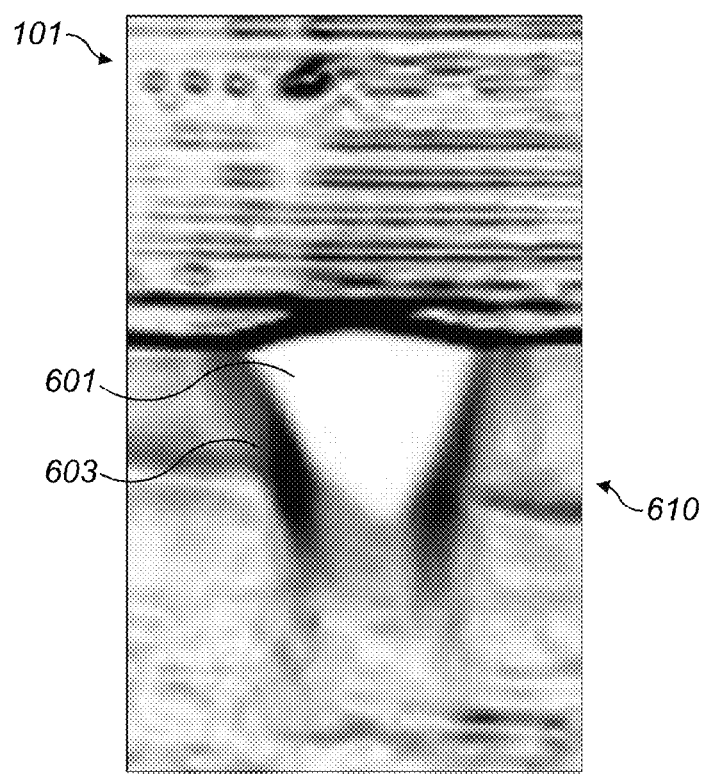
FIG. 7 is a photograph of a two-stage plasma plume generated by a plasma torch according to an embodiment of aspects of the invention, wherein edge detection algorithm has been applied to the image to help reveal the structure of the cooperative plume.

FIG. 7 shows a photograph of a two-stage plasma plume generated by a plasma torch 101 built according to the embodiment shown in FIG. 3. The photograph has been processed using edge detection algorithm which reveals the structure of the cooperative plume showing the focused, central thermal MHD blade 601 and the entrainment of the sterilising DBD non-thermal halo 603 to produce a collimated, cooperative two-stage plasma plume 610.

In order to use the plasma plume 610 for cosmetic or surgical treatment, the operator would initiate the plasma plume and move the tip of the plasma torch 101 along the treatment area of the tissue at a fixed distance, in a "paintbrush" fashion, to achieve the desired effect and outcome. This distance is controlled using disposable "patient interface tubes" that allow the user to see the area and the plume of the device. For cosmetic, non-surgical use of the plasma to reduce wrinkles and rejuvenate skin, the cosmetic treatments may be performed by appropriately trained, non-medical personnel (such as a cosmetic technician) in a non-medical setting as the treatment is non-invasive and poses minimal health risks and side effects as the plasma plume itself provides a sterile dressing. For purely cosmetic treatments, the operator need not be a skilled medical professional. However, for wound debridement and for stimulating regeneration of tissue for medically curative purposes, or for cauterisation in a surgical setting or as part of a wider surgical intervention, the two-stage plasma plume will need to be operated by a medical professional.

A trigger control (not shown) may be provided on the plasma torch to initiate the release of the feed gas and the activation of the power supply by the system control unit in order to produce the co-operative plume on-demand (or just the non-thermal plasma) by the operator. The apparatus may be configured such that the trigger mechanism may cause the plasma plume to be constantly generated for as long as the trigger is depressed. Alternatively, the apparatus may be configured such that a short blast or pulse of plasma is generated in response to depressing of the trigger. Repeated operation of the trigger may then be necessary in order to produce plasma pulses for use in cosmetic and surgical treatments. The energy to be delivered to the surface will be controlled on the base unit.

The description of the preferred embodiments of the present invention has been presented for purposes of illustration and description, but is not intended to be exhaustive or to limit the invention to the forms disclosed. It will be appreciated by those skilled in the art that changes could be made to the embodiments described above without departing from the broad inventive concept thereof. It is understood, therefore, that this invention is not limited to the particular embodiment disclosed, but covers modifications within the scope of the present invention as defined by the appended claims.

The invention claimed is:

1. A plasma torch having an open end from which a plasma plume is emitted in use, comprising:
    a central cathode rod;
    a grounded conductive tube having an open end and being arranged around the cathode and spaced therefrom to form a first cylindrical cavity open at one end in which, in use, an arc discharge between the cathode and grounded tube ionizes a feed gas to produce a central thermal plasma emitted from the open end of the first cavity;
    a high voltage electrode having a dielectric barrier material at a radially inward-facing surface thereof and being arranged around the grounded conductive tube and spaced apart therefrom to form a second annular cylindrical cavity open at one end in which, in use, a dielectric barrier discharge between the high voltage electrode and grounded tube ionizes a feed gas to produce at the open end of the second cavity a non-thermal plasma halo surrounding the central thermal plasma; and wherein the cathode is detachably connected to the torch as a part of a replaceable modular assembly; and wherein the high voltage electrode is detachably connected to the torch as a part of a replaceable modular assembly.

2. The plasma torch as claimed in claim of claim 1, wherein the end of the central cathode rod is recessed from an open end of the grounded lube such that, in use, the arc current causes a Lorentz force that accelerates the thermal plasma towards a focal point in front of the open end of the torch.

3. The plasma torch as claimed in claim 1, wherein the relative axial extent of the cathode and grounded tube at the open end of the plasma torch is configured such that the resulting plasma plume is concentrated a given focal distance in front of the open end of the torch.

4. The plasma torch as claimed in claim 1, wherein the cathode and grounded tube are relatively axially moveable to allow a user of the torch to adjust a local distance of the plasma plume.

5. The plasma torch as claimed in claim 1, wherein the cathode, grounded tube and high voltage electrode are arranged co-axially.

6. The plasma torch as claimed in claim 1, further comprising an annular permanent magnet arranged radially outwardly of the grounded tube at the open end thereof and configured to produce a magnetic torque on the arc discharge to cause the arc discharge, in use, to rotate around the cathode.

7. The plasma torch as claimed in claim 1, wherein at least the cathode, grounded tube and high voltage electrode are arranged such that, in use, the central thermal plasma collimates, and optionally entrains and/or focusses, at least some of the surrounding halo non-thermal plasma.

8. The plasma torch as claimed in claim 1, wherein the plasma torch is configured as a handpiece for an end user to hold and manipulate in use.

9. The plasma torch as claimed in claim 8, further comprising an ergonomic grip coupled to the handpiece to facilitate user operation.

10. The plasma torch as claimed in claim 9, comprising interchangeable ergonomic grips detachably coupleable to the handpiece, wherein optionally the interchangeable ergonomic grips include one or more of: a trigger grip; a tripod grip; a pen grip.

11. The plasma torch as claimed in claim 1, wherein the cathode and high voltage electrode are separately detachably connected to the torch as parts of separately replaceable modular assemblies.

12. The plasma torch as claimed in claim 1, wherein the grounded tube and cathode are together detachably connected to the torch as parts of a replaceable modular assemblies.

13. The plasma torch as claimed in claim 1, wherein the plasma torch and each modular assembly have mutually cooperating screw threads to enable the detachable connections therebetween.

14. The plasma torch as claimed in claim 1, further comprising: at least one feed gas inlet opening for each of the first and second cavities; wherein the plasma torch is configured to provide sealed fluid communication between each feed gas inlet and a feed gas connector for connecting to a feed gas supply.

15. The plasma torch as claimed in claim 14, wherein separate feed gas connectors are provided for each of the first and second cavities, and wherein the plasma torch is further configured such that fluid communication lines between the feed gas connectors and the feed gas inlets to the first and second cavities are sealed from each other, such that separate feed gases are in use supplied to the first and second cavities.

16. An electrical power generator unit coupled with an providing power in use to the plasma torch as claimed in claim 1, comprising: means configured to provide to the cathode in use a constant direct current (DC) electrical power supply plus a high voltage pulsed electrical power supply to initiate the arc discharge in the first cylindrical cavity; means configured to provide to the high voltage electrode in use a high voltage alternating current electrical power supply or pulsed electrical power supply to generate the dielectric barrier discharge in the second annular cylindrical cavity.

17. Apparatus for generating a plasma plume, comprising: the plasma torch; and the electrical power generator unit as claimed in claim 16 coupled to the plasma torch.

18. An Apparatus for generating a plasma plume as claimed in claim 17, further comprising one or more containers of feed gas connected to the plasma torch, wherein the apparatus is configured such that feed gas is supplied to the first and second cavities to be ionized in use.

19. A modular cathode assembly in the plasma torch as claimed in in claim 1, comprising a cathode and optionally a grounded tube and being configured to be detachably connectable to the plasma torch to enable the cathode thereof to be replaced.

20. A modular high voltage electrode assembly in the plasma torch as claimed in claim 1, comprising a high voltage electrode and being configured to be detachably connectable to the plasma torch to enable the high voltage electrode thereof to be replaced.

21. Use of the plasma torch as claimed in in claim 1 in the non-surgical cosmetic treatment of skin, optionally for one or more of: wrinkle removal; skin resurfacing; skin ablation; scar removal; hair removal; treatment of Rosacea; treatment of acne.

22. Use of the plasma torch as claimed in claim 1 in non-surgical treatment.

23. Use of the plasma torch as claimed in claim 1 in surgical treatment of live tissue, optionally for one or more of: cauterization; tissue ablation for wound healing; wound or bumn sterilization; cavity sterilization.

* * * * *

UNITED STATES PATENT AND TRADEMARK OFFICE
CERTIFICATE OF CORRECTION

PATENT NO. : 10,595,391 B2
APPLICATION NO. : 15/524344
DATED : March 17, 2020
INVENTOR(S) : Aaron Knoll et al.

Page 1 of 1

It is certified that error appears in the above-identified patent and that said Letters Patent is hereby corrected as shown below:

In the Claims

Column 19, Claim 2, Line 15, delete "lube" and insert -- tube --.

Column 19, Claim 4, Line 26, delete "local" and insert -- focal --.

Column 20, Claim 18, Line 33, delete "Apparatus" and insert -- apparatus --.

Column 20, Claim 23, Line 58, delete "bumn" and insert -- burn --.

Signed and Sealed this
Twelfth Day of May, 2020

Andrei Iancu
*Director of the United States Patent and Trademark Office*